US00PP36391P2

(12) United States Plant Patent
Fieldes

(10) Patent No.: US PP36,391 P2
(45) Date of Patent: Jan. 14, 2025

(54) ***SENECIO* PLANT NAMED 'Sennova Mi RL'**

(50) Latin Name: *Senecio candidans*
Varietal Denomination: Sennova Mi RL

(71) Applicant: Flowerzone International Ltd, Auckland (NZ)

(72) Inventor: Lyall Fieldes, Whangerei (NZ)

(73) Assignee: FLOWERZONE INTERNATIONAL LTD, Auckland (NZ)

( * ) Notice: Subject to any disclaimer, the term of this patent is extended or adjusted under 35 U.S.C. 154(b) by 0 days.

(21) Appl. No.: 18/640,104

(22) Filed: Apr. 19, 2024

(30) Foreign Application Priority Data

Jan. 12, 2024 (QZ) ..... PBR 20240052

(51) Int. Cl.
*A01H 5/02* (2018.01)
*A01H 6/14* (2018.01)

(52) U.S. Cl.
USPC ..... Plt./480

(58) Field of Classification Search
USPC ..... Plt./263.1, 480
See application file for complete search history.

*Primary Examiner* — Karen M Redden
(74) *Attorney, Agent, or Firm* — Penny J. Aguirre

(57) ABSTRACT

A new cultivar of *Senecio* plant named 'Sennova Mi RL' that is characterized by its compact plant habit (20 cm in height and spread), its leaves that are silvery white and green in color and fading to green, and its leaves that are broadly ovate to broadly oblong in shape.

2 Drawing Sheets

Botanical classification: *Senecio candidans*.
Variety denomination: 'Sennova Mi RL'.

BACKGROUND OF THE INVENTION

The present invention relates to a new and distinct cultivar of *Senecio* plant, botanically known as *Senecio candidans* 'Sennova Mi RL' and will be referred to hereafter by its cultivar name, 'Sennova Mi RL'. The new cultivar represents a new sea cabbage grown as an ornamental used for landscape and container use.

The Inventor discovered the new cultivar in summer of 2020 as a naturally occurring branch mutation of *Senecio* 'Angel Wings' (not patented) that was growing in a greenhouse in a container in Hachimantai, Iwate, Japan.

Asexual propagation of the new cultivar was first accomplished by stem cuttings in Hachimantai, Iwate, Japan in April of 2021 by the Inventor. Asexual propagation by stem cuttings and tissue culture using meristematic tissue has determined that the characteristics of this cultivar are stable and are reproduced true to type in successive generations.

SUMMARY OF THE INVENTION

The following traits have been repeatedly observed and represent the characteristics of 'Sennova Mi RL'. These attributes in combination distinguish 'Sennova Mi RL' as a new and distinct cultivar of *Senecio*.

1. 'Sennova Mi RL' exhibits a compact plant habit (20 cm in height and spread).
2. 'Sennova Mi RL' exhibits leaves that are silvery white and green in color and fading to green.
3. 'Sennova Mi RL' exhibits leaves that are broadly ovate to broadly oblong in shape.

The parent plant of 'Sennova Mi RL' differs from 'Sennova Mi RL' in having a less compact plant habit and leaves that are larger in size, round to cordate in shape, and more silvery white in color. 'Sennova Mi RL' can also be compared to cultivars *Senecio niveoaureus* 'Silver Feathers' (not patented) and *Senecio candidans* 'Angel Baby'. 'Silver Feathers' is similar to 'Sennova Mi RL' in having silver foliage that is covered with woolly pubescent hairs. 'Silver Feathers' differs from 'Sennova Mi RL' in having leaves that are more linear in shape, become limp, and are less thick. 'Angel Baby' is similar to 'Sennova Mi RL' in having foliage that is silvery white with green in color and is covered with woolly pubescent hairs. 'Angel Baby' differs from 'Sennova Mi RL' in having a slightly smaller plant size and leaves that are oval in shape and slightly curly.

BRIEF DESCRIPTION OF THE DRAWINGS

The accompanying color photographs illustrates the overall appearance and distinct characteristics of the new *Senecio*. The photographs were taken of a 1-year-old plant of 'Sennova Mi RL' as grown in an unheated conventional greenhouse in a 15-cm container in Berkel en Rodenrijs, The Netherlands.

The photograph in FIG.1 provides a side view of a plant of 'Sennova Mi RL'.

Figure 1:
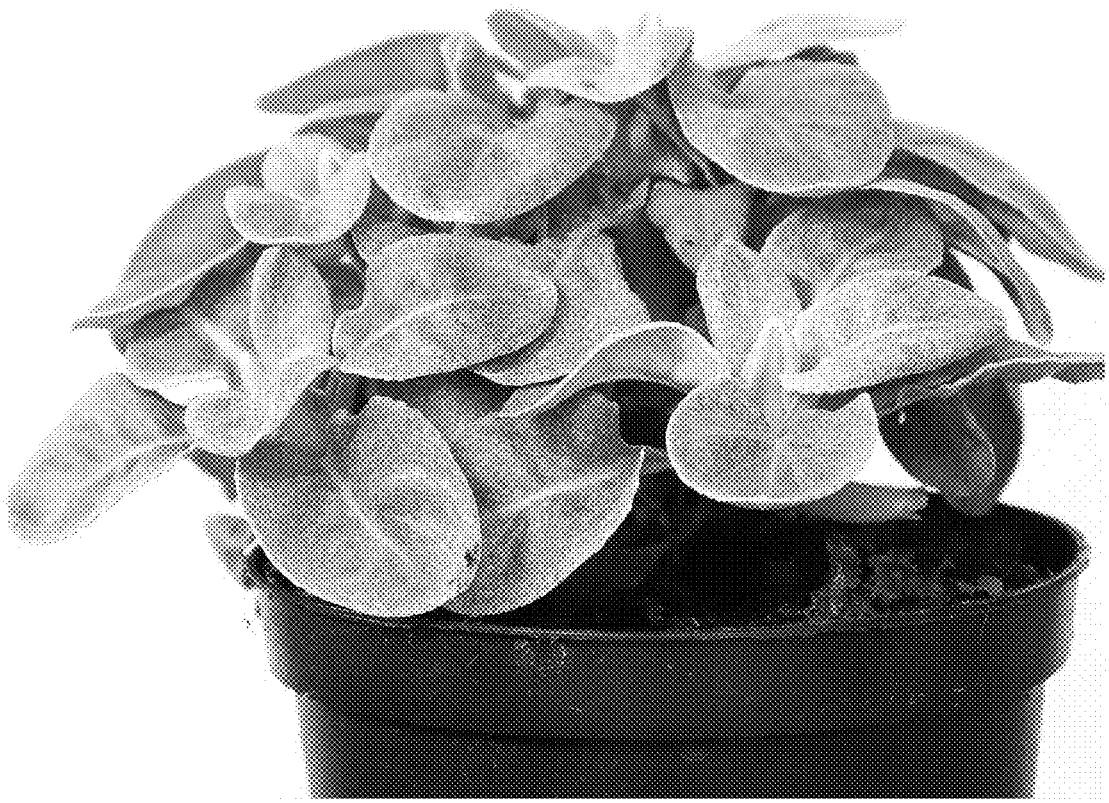
Figure 2:
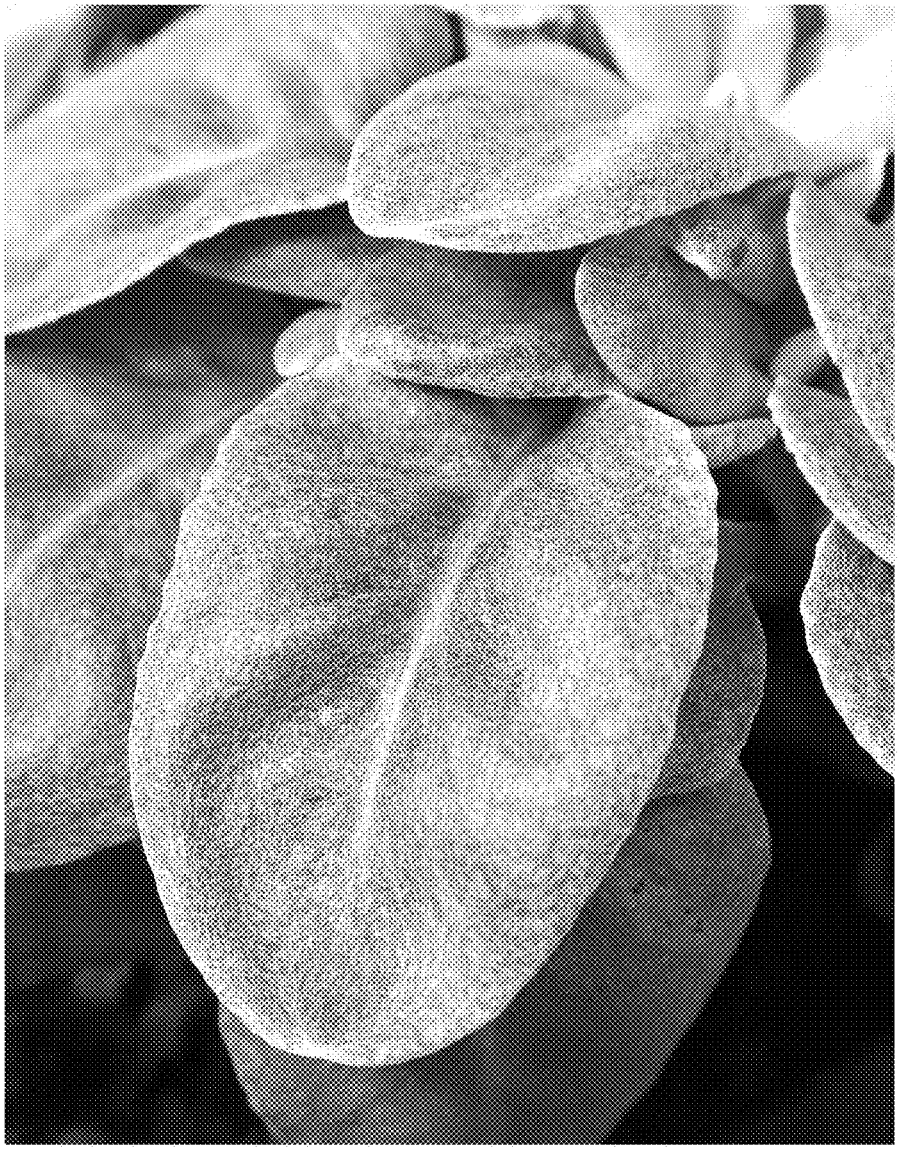

The photograph in FIG. 2 is a close-up view of the foliage of 'Sennova Mi RL'.

The colors in the photographs may differ slightly from the color values cited in the detailed botanical description, which accurately describe the colors of the new *Senecio*.

DETAILED BOTANICAL DESCRIPTION

The following is a detailed description of 1-year-old plants of the new cultivar as grown in 15-cm containers in an unheated conventional greenhouse in Berkel en Rodenrijs, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Plant type*.—Evergreen perennial.

*Plant habit*.—Compact, flattened globular, upright and broadly spreading.

*Height and spread*.—An average of 11 cm in height and 20 cm in width as a one-year-old plant as grown in a container, reaches 20 in height and width when grown in the landscape.

*Hardiness*.—At least to U.S.D.A. Zones 8 to 11.

*Diseases and pests*.—No susceptibility or resistance to diseases or pests has been observed.

*Root description*.—Fibrous.

*Propagation*.—Stem cuttings and tissue culture.

*Time required for root development*.—An average of 2 to 4 weeks for root initiation and 3 to 5 months to fully root as a young plant.

*Growth rate*.—Moderately vigorous.

Stem description:

*Stem shape*.—Rounded.

*Stem color*.—Young; 146D, mature; 147C and 148C.

*Stem size*.—Average of 6.5 cm in length and 5 mm in diameter.

*Stem surface*.—Matte, densely covered with woolly pubescence 192D in color.

*Branching*.—Main; 1, lateral branches; 8.

*Aspect*.—Main; 80° from horizontal, lateral; 70° to main.

*Internode length*.—Average of 7 mm.

Foliage description:

*Leaf division*.—Simple.

*Leaf arrangement*.—Alternate.

*Leaf shape*.—Broadly ovate to broadly oblong.

*Leaf size*.—Average of 6.2 cm in length and 4.7 cm in width.

*Leaf number*.—Average of 10 per lateral branch.

*Leaf base*.—Short attenuate.

*Leaf apex*.—Obtuse.

*Leaf margin*.—Entire; shallow dentate at the base, with blunt teeth, undulation low to none.

*Leaf aspect*.—Slightly convex.

*Leaf venation*.—Pinnate, upper veins color; 146D, densely covered with woolly pubescent hairs 192D in color, lower veins color; 145B, densely covered with woolly pubescent hairs 192D and 192D in color.

*Leaf color*.—Young upper surface; 137C, densely covered with woolly pubescent hairs a blend of N155A and 192D, young lower surface; 137D, densely covered with woolly pubescent hairs a blend of N155A and 192D, mature upper surface; 137B, densely covered with woolly pubescent hairs 192D, mature lower surface; 138B, densely covered with woolly pubescent hairs a blend of 192C and 192D.

*Leaf surface*.—Both surfaces; densely pubescent and matte.

*Leaf substance*.—Leathery.

*Petioles*.—Strong, average of 3.9 cm in length, flattened, diameter at widest point 1 cm, at narrowest point 3 mm, upper surface glabrous, slightly glossy, and velvety, lower surface pubescent, matte, densely covered with woolly pubescence, 192D in color, color; upper surface 148D, margins 144A, lower surface 146D.

*Foliage fragrance*.—Mild mint scent if crushed.

Flower description: No flowers observed to date.

It is claimed:

1. A new and distinct variety of *Senecio* plant named 'Sennova Mi RL' as described and illustrated herein.

* * * * *